US012558388B2

(12) United States Patent
Zhou et al.

(10) Patent No.: US 12,558,388 B2
(45) Date of Patent: Feb. 24, 2026

(54) USE OF RADIX ACTINIDIAE CHINENSIS AND EXTRACT THEREOF IN PREPARATION OF MEDICINE FOR TREATING ULCERATIVE COLITIS

(71) Applicant: Affiliated Hospital of Guangdong Medical University, Zhanjiang (CN)

(72) Inventors: Yu Zhou, Zhanjiang (CN); Lijiao Cui, Zhanjiang (CN); Caiyuan Yu, Zhanjiang (CN); Shicai Ye, Zhanjiang (CN)

(73) Assignee: Affiliated Hospital of Guangdong Medical University, Zhanjiang (CN)

( * ) Notice: Subject to any disclaimer, the term of this patent is extended or adjusted under 35 U.S.C. 154(b) by 224 days.

(21) Appl. No.: 18/411,067

(22) Filed: Jan. 12, 2024

(65) Prior Publication Data

US 2024/0342232 A1 Oct. 17, 2024

(30) Foreign Application Priority Data

Apr. 14, 2023 (CN) .......................... 202310400802.0

(51) Int. Cl.
*A61K 36/185* (2006.01)
*A61P 1/00* (2006.01)

(52) U.S. Cl.
CPC .............. *A61K 36/185* (2013.01); *A61P 1/00* (2018.01); *A61K 2236/331* (2013.01)

(58) Field of Classification Search
CPC ........... A61K 36/185; A61K 2236/331; A61K 2236/33; A61K 9/0031; A61K 9/0053; A61P 1/00; A61P 1/04; Y02A 50/30; G01N 2800/065; G01N 2800/067
See application file for complete search history.

(56) References Cited

FOREIGN PATENT DOCUMENTS

| CN | 1003108 | B | * | 1/1989 | |
|----|---------|---|---|--------|---|
| CN | 101757056 | A | | 6/2010 | |
| CN | 101164558 | B | * | 12/2011 | |
| CN | 102688266 | A | * | 9/2012 | |
| CN | 102784284 | A | * | 11/2012 | |
| CN | 102839108 | B | * | 12/2013 | |
| CN | 104042530 | A | * | 9/2014 | |
| CN | 104825507 | A | | 8/2015 | |
| CN | 104984204 | A | | 10/2015 | |
| CN | 116381071 | A | * | 7/2023 | ............. G01N 30/02 |

OTHER PUBLICATIONS

Xiao W, et al, machine translation of et al, machine translation of CN 101164558 B, 62 pages (Year: 2011).*
Zhao Y, et al, machine translation of CN 116381071 A, 3 pages. (Year: 2023).*
Wan J, machine translation of CN 104042530 A, 7 pages. (Year: 2014).*
Wang S, et al, machine translation of CN 102839108 B, 11 pages. (Year: 2013).*
Wang H, et al, machine translation of CN 102784284 A, 16 pages. (Year: 2012).*
Teng K, et al, machine translation of CN 102688266 A, 15 pages (Year: 2012).*
Xiao W, et al, machine translation of CN 101164558 B, 62 pages (Year: 2011).*
Zhang S, et al, machine translation of CN 1003108 B, 16 pages. (Year: 1989).*
Yanhua Sui, et al., Studies on the pharmacological effects of kiwi root, Journal of Guiyang College of Traditional Chinese Medicine, 1991, pp. 60-64, vol. 1.
Pian Shen, Pharmacology and Clinics of Chinese Medicines, Jilin Science and Technology Press, 2020, pp. 971, 953, vol. 2.

* cited by examiner

*Primary Examiner* — Aaron J Kosar
(74) *Attorney, Agent, or Firm* — Bayramoglu Law Offices LLC

(57) ABSTRACT

Use of radix actinidiae chinensis and an extract thereof in preparation of a medicine for treating ulcerative colitis are provided. The radix actinidiae chinensis extract is a radix actinidiae chinensis water extract or a radix actinidiae chinensis alcohol extract. The radix actinidiae chinensis extract has an obvious anti-inflammatory effect on the ulcerative colitis; and because the radix actinidiae chinensis extract has the obvious anti-inflammatory effect on the ulcerative colitis, the radix actinidiae chinensis serving as a raw material also has an obvious anti-inflammatory effect on the ulcerative colitis. Moreover, the radix actinidiae chinensis is widely distributed in China, and is widely cultivated in Shaanxi and other regions. Moreover, the radix actinidiae chinensis is a traditional Chinese medicine for clearing away heat and toxic materials, and its toxic and side effects are small.

9 Claims, 3 Drawing Sheets

USE OF RADIX ACTINIDIAE CHINENSIS AND EXTRACT THEREOF IN PREPARATION OF MEDICINE FOR TREATING ULCERATIVE COLITIS

CROSS REFERENCE TO THE RELATED APPLICATIONS

This application is based upon and claims priority to Chinese Patent Application No. 202310400802.0, filed on Apr. 14, 2023, the entire contents of which are incorporated herein by reference.

TECHNICAL FIELD

The present invention relates to the technical field of medicaments, and particularly relates to use of a radix actinidiae chinensis extract in preparation of a medicine for treating ulcerative colitis and use of radix actinidiae chinensis in preparation of a medicine for treating ulcerative colitis.

BACKGROUND

At present, commonly used medicines for the clinical treatment of ulcerative colitis (UC) mainly include amino-salicylic acids, immunosuppressants, steroids and some biological agents, etc. These medicines can achieve remission of the disease to a certain extent, but in terms of long-term maintenance of remission, promotion of deep mucosal healing, recurrence prevention, etc., these medicines are not satisfactory in efficacy and are usually expensive in cost. Long-term maintenance of medication will consume a lot of medical resources and will also cause many adverse reactions.

Mesalazine is a most commonly used medicine for treating ulcerative colitis and is mainly used in UC patients with mild or moderate conditions in an active stage or maintenance of a remission stage. A main active ingredient of mesalazine is 5-aminosalicylic acid. Since the ulcerative colitis is a chronic and refractory disease, long-term maintenance of mesalazine taking will not only bring an economic burden to patients and their families, but also cause adverse reactions, ranging from mild stomach discomfort to chronic hepatitis. Therefore, patients who take mesalazine for a long time need to frequently check liver indicators-alanine aminotransferase (ALT), etc. If the indicator far exceeds the normal level, the patients need to stop taking the mesalazine, otherwise hepatitis, liver fibrosis and even liver necrosis will be caused easily.

Therefore, aiming at the shortcomings in the prior art, it is necessary to provide the use of the radix actinidiae chinensis extract in the preparation of the medicine for treating ulcerative colitis and the use of the radix actinidiae chinensis in the preparation of the medicine for treating ulcerative colitis.

SUMMARY

One of the objects of the present invention is to avoid the shortcomings in the prior art and provide use of a radix actinidiae chinensis extract in preparation of a medicine for treating ulcerative colitis. The radix actinidiae chinensis extract has an obvious anti-inflammatory effect on ulcerative colitis.

The above object of the present invention is achieved through the following technical measures:

Provided is use of a radix actinidiae chinensis extract in preparation of a medicine for treating ulcerative colitis.

Preferably, the radix actinidiae chinensis extract is a radix actinidiae chinensis water extract or a radix actinidiae chinensis alcohol extract.

When the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells.

When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

Preferably, the ulcerative colitis is inhibited by the radix actinidiae chinensis extract by means of decreasing a degree of colorectal shortening.

Preferably, the ulcerative colitis is inhibited by the radix actinidiae chinensis extract by means of reducing a degree of occult blood production.

Preferably, the ulcerative colitis is inhibited by the radix actinidiae chinensis extract by means of decreasing a degree of weight loss.

In the present invention, the radix actinidiae chinensis extract is dissolved in water, and the concentration is 20 μg/ml to 300 μg/ml.

A route of administration of the present invention is to decoct a traditional Chinese medicinal material of the radix actinidiae chinensis with water to obtain the radix actinidiae chinensis extract, and take it orally or use it as an enema, or a route of administration of the present invention is to take a finished product of the radix actinidiae chinensis extract or dissolve it and then use it as an enema.

Another object of the present invention is to avoid the shortcomings in the prior art and provide use of radix actinidiae chinensis in preparation of a medicine for treating ulcerative colitis. The radix actinidiae chinensis extract has an obvious anti-inflammatory effect on ulcerative colitis.

The above object of the present invention is achieved through the following technical measures:

Provided is use of radix actinidiae chinensis in preparation of a medicine for treating ulcerative colitis.

The present invention relates to use of radix actinidiae chinensis and a radix actinidiae chinensis extract in preparation of a medicine for treating ulcerative colitis. The radix actinidiae chinensis extract has an obvious anti-inflammatory effect on ulcerative colitis; and because the radix actinidiae chinensis extract has an obvious anti-inflammatory effect on ulcerative colitis, the radix actinidiae chinensis as a raw material also has an obvious anti-inflammatory effect on ulcerative colitis. Moreover, the radix actinidiae chinensis is widely distributed in China, and is widely cultivated in Shaanxi and other regions. Moreover, the radix actinidiae chinensis is a traditional Chinese medicine for clearing away heat and toxic materials, and its toxic and side effects are small. Therefore, when using the radix actinidiae chinensis and the radix actinidiae chinensis extract as a medicine for ulcerative colitis, the treatment cost can be greatly decreased, the treatment of ulcerative colitis is effective, and the toxic and side effects are small after long-term taking.

BRIEF DESCRIPTION OF THE DRAWINGS

The present invention is further described using the accompanying drawings, but the contents in the accompanying drawings do not constitute any limitation on the present invention.

DETAILED DESCRIPTION OF THE EMBODIMENTS

Figure 1:
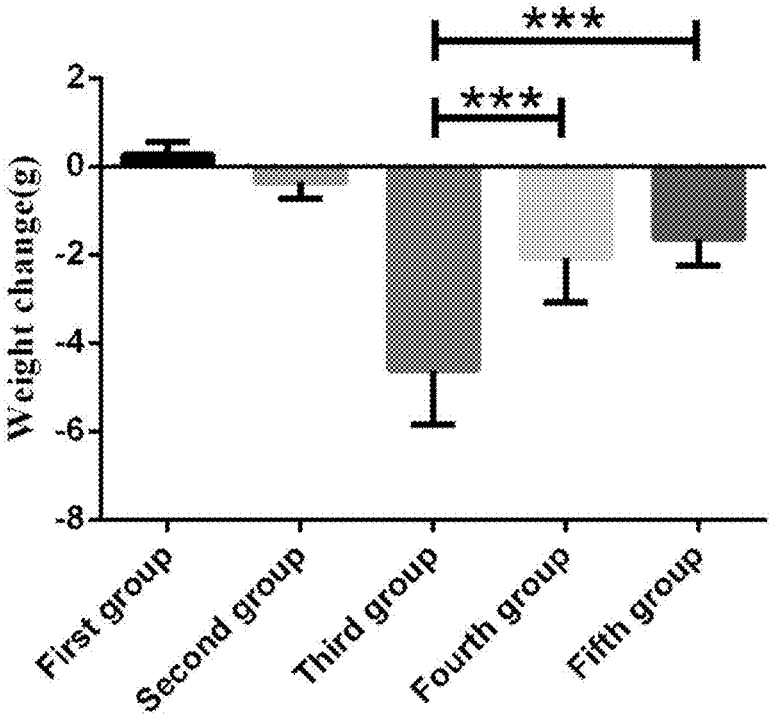
FIG. 1 shows an effect of a radix actinidiae chinensis extract on body weights of mice.

The technical solution of the present invention will be further described with reference to the following embodiments.

The experimental methods in the following embodiments are all conventional methods unless otherwise specified. The raw materials, reagent materials, etc. used in the following embodiments can be purchased from conventional biochemical reagent stores or pharmaceutical trading enterprise unless otherwise specified.

Embodiment 1

Provided is use of a radix actinidiae chinensis extract in preparation of a medicine for treating ulcerative colitis, wherein radix actinidiae chinensis is an extract of the radix actinidiae chinensis.

The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was within the range of 20 μg/ml to 300 μg/ml, the anti-inflammatory effect was obvious.

It should also be pointed out that the radix actinidiae chinensis is the dried root of *Actinidia chinensis* Planch or *A. arguta* Planch, etc. in the actinidiaceae plant. The radix actinidiae chinensis is bitter, astringent, cool in nature and non-toxic. It is a traditional Chinese medicine for clearing away heat and toxic materials. It has the functions of clearing away heat and toxic materials, promoting blood circulation and reducing swelling, dispelling wind, removing dampness, stopping bleeding, relieving inflammation, resisting cancer, etc. It is mainly used to treat indigestion, vomiting, rheumatic arthralgia, digestive tract tumors, carbuncle, ulcer, sore, furuncle, etc.

There are a wide variety of compounds in the radix actinidiae chinensis. According to literature reports, more than 290 compounds have been isolated from the radix actinidiae chinensis, mainly including triterpenes, flavonoids, phenolic acids, phenylpropanoids, anthraquinones, alkaloids, steroids, organic acids, etc. Wherein, the main active ingredients are pentacyclic triterpenes, followed by flavonoids, phenolic acids, phenylpropanoids, etc. Catechin derivatives, coumarin derivatives and phenolic acid derivatives are the main water-soluble components of the radix actinidiae chinensis.

The applicant also used network pharmacology to collect and screen the active ingredients of the radix actinidiae chinensis: through the Traditional Chinese Medicine Systems Pharmacology Database and Analysis Platform (TCMSP, https://old.tcmsp-e.com/tcmsp.php), query the chemical composition of the radix actinidiae chinensis in the database, and then screen the main active ingredients of the radix actinidiae chinensis under the conditions of oral availability (OB) ≥30% and medicine-likeness (DL) ≥0.18. By querying the database, a total of 26 active ingredients of the radix actinidiae chinensis were collected. Under the conditions of oral availability (OB) ≥30% and medicine-likeness (DL) ≥0.18, 6 main chemical compositions were screened, as shown in Table 1.

TABLE 1

| List of main active ingredients of radix actinidiae chinensis | | | | |
|---|---|---|---|---|
| MOL ID | Molecule name | Chinese name | OB (%) | DL |
| MOL000073 | ent-Epicatechin | ent-Epicatechin | 48.96 | 0.24 |
| MOL000098 | quercetin | quercetin | 46.43 | 0.28 |
| MOL000358 | beta-sitosterol | beta-sitosterol | 36.91 | 0.75 |
| MOL000359 | sitosterol | sitosterol | 36.91 | 0.75 |
| MOL000471 | aloe-emodin | aloe-emodin | 83.38 | 0.24 |
| MOL000492 | (+) - catechin | (+) - catechin | 54.83 | 0.24 |

The 6 compounds in the above table are the main chemical compositions of the radix actinidiae chinensis. The radix actinidiae chinensis water extract of the present invention was extracted from the radix actinidiae chinensis with water, while the radix actinidiae chinensis alcohol extract was extracted from the radix actinidiae chinensis with alcohols such as methanol and ethanol. The radix actinidiae chinensis water extract and the radix actinidiae chinensis alcohol extract are common extraction methods and preparation methods for the radix actinidiae chinensis for those skilled in the art, so the extraction methods will not be described in detail here. For different water extraction or alcohol extraction methods, such as different extraction temperatures and extraction solvent properties, it is possible to extract the radix actinidiae chinensis water extract or the radix actinidiae chinensis alcohol extract containing the 6 compounds in the table as the main components. There are only deviations in impurities or content, and these deviations do not affect the anti-inflammatory effect on ulcerative colitis. The applicant conducted analysis through network pharmacology and bioinformatics methods, and the analysis showed that the intersection targets of the radix actinidiae chinensis and the UC are related to UC-related molecular functions and biological processes such as IL-4, IL-13, IL-18, and inflammatory response; and at the same time, the intersection targets are closely related to classic UC-related signaling pathways such as PI3K-Akt, NF-κB, JAK-STAT, TGF-β, and AMPK. The effect of the present application is related to these 6 compounds.

In summary, the radix actinidiae chinensis extract has an obvious anti-inflammatory effect on ulcerative colitis and can be used to prepare medicines for treating ulcerative colitis. Therefore, when using the radix actinidiae chinensis extract as a medicine for treating ulcerative colitis, the treatment cost can be greatly decreased, the treatment of ulcerative colitis is effective, and the toxic and side effects are small after long-term taking.

Embodiment 2

Provided is use of a radix actinidiae chinensis extract in the preparation of a medicine for treating ulcerative colitis. The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was within the range of 50 μg/ml to 200 μg/ml, the anti-inflammatory effect was obvious.

In Embodiment 1, the radix actinidiae chinensis extract in the present embodiment has a better anti-inflammatory effect on ulcerative colitis and can be used to prepare a medicine for treating ulcerative colitis.

Embodiment 3

Provided is use of a radix actinidiae chinensis extract in the preparation of a medicine for treating ulcerative colitis. The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was 20 μg/ml, the anti-inflammatory effect was obvious.

In Embodiment 1, the radix actinidiae chinensis extract in the present embodiment has a better anti-inflammatory effect on ulcerative colitis and can be used to prepare a medicine for treating ulcerative colitis.

Embodiment 4

Provided is use of a radix actinidiae chinensis extract in the preparation of a medicine for treating ulcerative colitis. The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was 300 μg/ml, the anti-inflammatory effect was obvious.

In Embodiment 1, the radix actinidiae chinensis extract in the present embodiment has a better anti-inflammatory effect on ulcerative colitis and can be used to prepare a medicine for treating ulcerative colitis.

Embodiment 5

Provided is use of a radix actinidiae chinensis extract in the preparation of a medicine for treating ulcerative colitis. The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was 50 μg/ml, the anti-inflammatory effect was obvious.

In Embodiment 1, the radix actinidiae chinensis extract in the present embodiment has a better anti-inflammatory effect on ulcerative colitis and can be used to prepare a medicine for treating ulcerative colitis.

Embodiment 6

Provided is use of a radix actinidiae chinensis extract in the preparation of a medicine for treating ulcerative colitis. The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was 100 μg/ml, the anti-inflammatory effect was obvious.

In Embodiment 1, the radix actinidiae chinensis extract in the present embodiment has a better anti-inflammatory effect on ulcerative colitis and can be used to prepare a medicine for treating ulcerative colitis.

Embodiment 7

Provided is use of a radix actinidiae chinensis extract in the preparation of a medicine for treating ulcerative colitis.

The radix actinidiae chinensis extract of the present invention is a radix actinidiae chinensis water extract or a radix actinidiae chinensis alcohol extract.

The radix actinidiae chinensis extract of the present invention decreases a degree of colorectal shortening, reduces a degree of occult blood production, or decreases a degree of weight loss, thereby inhibiting the ulcerative colitis.

The applicant further studied and found that when the radix actinidiae chinensis extract is the radix actinidiae chinensis water extract, the ulcerative colitis is inhibited by decreasing secretion of at least one of an inflammatory factor IL-8, an inflammatory factor IL-17 or an inflammatory factor TNFα in intestinal epithelial cells. When the radix actinidiae chinensis extract is the radix actinidiae chinensis alcohol extract, the ulcerative colitis is inhibited by decreasing secretion of at least one of the inflammatory factor IL-8 or the inflammatory factor TNFα in the intestinal epithelial cells.

An NCM460 cell line was treated with different concentrations of radix actinidiae chinensis extracts, the effects of the radix actinidiae chinensis extracts on the expression of inflammatory factors in the intestinal epithelial cells were observed, and it was found through experiments that when the radix actinidiae chinensis extracts were dissolved in water and a concentration was 200 μg/ml, the anti-inflammatory effect was obvious.

In Embodiment 1, the radix actinidiae chinensis extract in the present embodiment has a better anti-inflammatory effect on ulcerative colitis and can be used to prepare a medicine for treating ulcerative colitis.

Embodiment 8

In order to elucidate the inhibitory effect and mechanism of the radix actinidiae chinensis extract on ulcerative colitis, a series of experimental studies were conducted, as follows:
1. Construction of UC Mouse Model 6-week-old SPF grade male BALB/c mice were selected, and each mouse weighed approximately 20 g. They were all healthy and had similar general conditions. They were raised under standard laboratory conditions (sterile diet, 50% air humidity, indoor temperature of 23° C. to 24° C., and a 12-hour day-night cycle), with free access to food and water. The animal raising and experimental processes complied with animal welfare and regulatory guidelines.

Grouping of mice and construction of a UC mouse model induced by dextran sulfate sodium (DSS) salt: the mice were randomly divided into 5 groups, with 8 mice in each group. The normal control group drank double-distilled water continuously; the UC mouse model group used a 3% DSS solution prepared with the double-distilled water and allowed the mice to drink it continuously, a total of 4 groups. Specifically, in these 5 groups of experiments, raising bottles containing the double-distilled water or the 3% DSS solution were placed directly on the mouse cages, and the mice drank by themselves.

Under the same conditions in the specific embodiment, the normal control group is the first group, and this group is only fed with the double-distilled water. The second to fifth groups are UC mouse models, wherein the second group of mice were only fed with the 3% DSS; the third group of mice were fed with the 3% DSS and 1 ml of the double-distilled water was given by gavage at the same time every day; the fourth group of mice were fed with the 3% DSS and 1 ml of radix actinidiae chinensis water extract with a concentration of 4 mg/ml was given by gavage at the same time every day;

and the fifth group of mice were fed with the 3% DSS and 1 ml of radix actinidiae chinensis alcohol extract with a concentration of 4 mg/ml was given by gavage at the same time every day. Clinical pathological indicators such as mouse weights, hemafecia, and activity indexes at different time periods were observed and recorded.

For the construction of the UC mouse model, the UC mouse model was treated with a certain concentration of radix actinidiae chinensis water extract (WE-acRoots) and radix actinidiae chinensis alcohol extract (AE-acRoots), and blood in the stool, body weights of the mice and other clinical indicators were detected at different time periods. Referring to the relevant literature, the experiment was generally completed after 10 to 14 days after modeling. When a model mouse died naturally after 10 days, all other mice would be killed by cervical dislocation. If no mice died after 14 days, they would be killed by cervical dislocation on the 14th day, and the mice were then dissected and the entire colorectum of the mice was removed, and the colorectum lengths of the mice was measured, as shown in FIG. 1 to FIG. 3.

Figure 2:
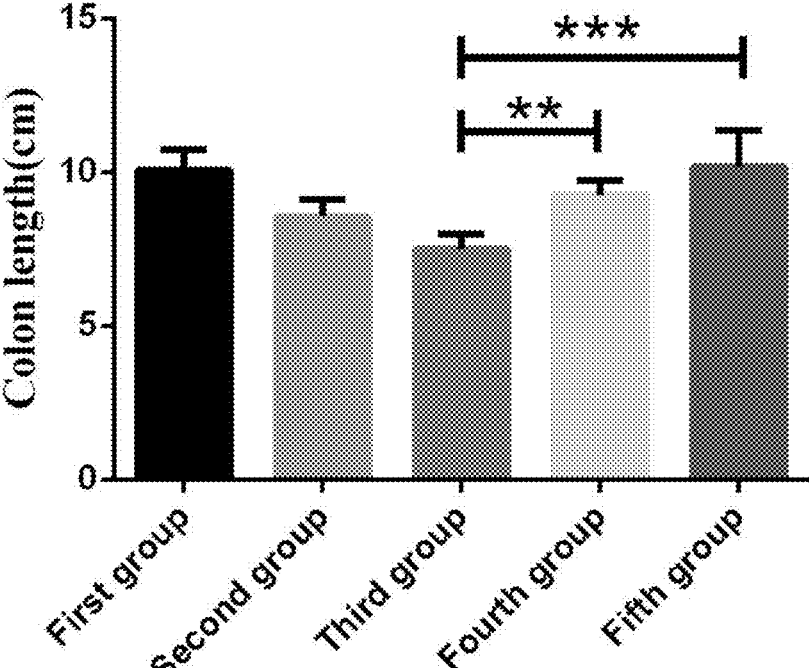
FIG. 2 shows an effect of the radix actinidiae chinensis extract on colon lengths of mice.
Figure 3:
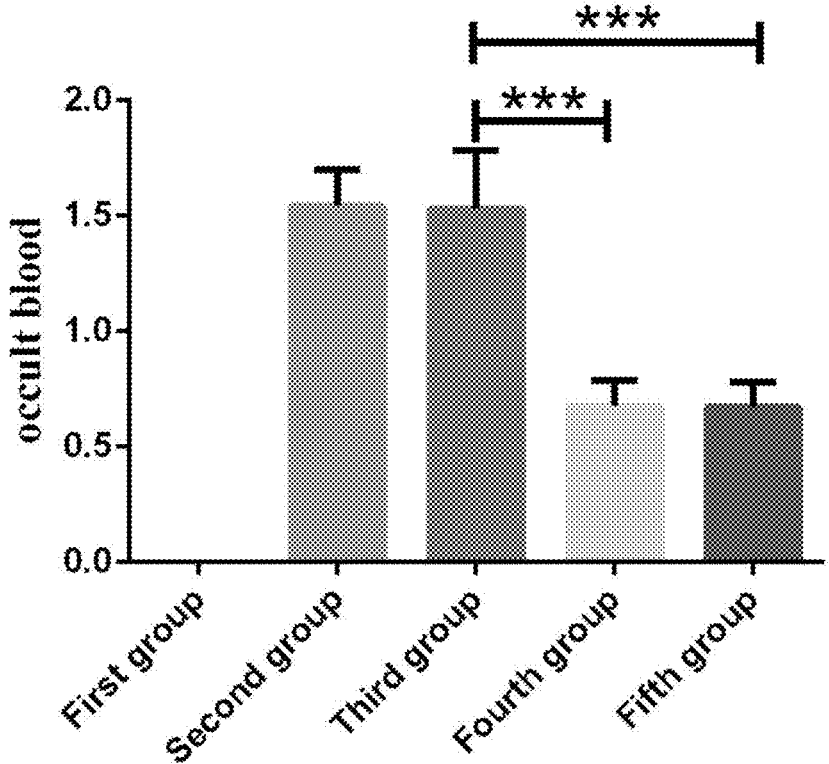
FIG. 3 shows an effect of the radix actinidiae chinensis extract on degrees of occult blood of mice.

The results from FIG. 1 to FIG. 3 show that both the radix actinidiae chinensis water extract and the radix actinidiae chinensis alcohol extract can significantly reduce the weight loss of mice (FIG. 1); reduce the shortening of the colon (FIG. 2) and reduce the severity of occult blood (FIG. 3), thus indicating that the radix actinidiae chinensis water extract and the radix actinidiae chinensis alcohol extract have a protective effect on the UC.

2. Effect of Radix Actinidiae Chinensis Extract on Inflammatory Factors in Cells (1) NCM460 Cell Line Treatment Use an RPMI1640 culture medium, add a 10% fetal bovine serum (FBS) to the culture medium, and cultivate routinely in a 37° C. incubator containing 5% $CO_2$ according to experimental requirements. Inoculate the NCM460 cell line into a 12-well plate and culture for 24 hours.

(2) Preparation of Different Concentrations of Radix Actinidiae Chinensis Extracts Dissolve 25 mg of water extract powder of the radix actinidiae chinensis and alcohol extract powder of the radix actinidiae chinensis in 500 μl of DEPC water, and then filter with a 0.22 μm microporous membrane to remove impurities such as bacteria and particles; add the RPMI 1640 culture medium containing 10% fetal calf serum to 25 ml in a filtrate, that is, the concentration of the mother solution of the radix actinidiae chinensis water extract and the radix actinidiae chinensis alcohol extract is 1 mg/ml; and then prepare the water extract of the radix actinidiae chinensis and the ethanol extract of the radix actinidiae chinensis into final concentrations of 0, 50 μg/ml, 100 μg/ml and 200 μg/ml with the RPMI 1640 culture medium containing the 10% fetal calf serum, respectively.

Treat NCM460 cells with different concentrations of radix actinidiae chinensis water extracts (WE-acRoots) and radix actinidiae chinensis alcohol extracts (AE-acRoots), respectively, and then continue to cultivate for 22 hours. Finally, use TNFα to induce cellular inflammation, add 5 μl of TNFα at a concentration of 10 μg/ml to each well of a 12-well plate to stimulate inflammation, after 2 hours, take out the cell culture plate and transfer the supernatant in the well plate in a 1.5 ml new sterile EP tube.

(3) ELISA Detects the Expression of Inflammatory Factors IL-8, IL-17, and TNFα

Details are as follows:

Step 3.1. Take out the cell culture plate, collect the cell supernatant in a 1.5 ml sterile EP tube, centrifuge at 3000 rpm for 10 min, transfer the supernatant to a 1.5 ml new sterile EP tube, and store at −80° C.

Step 3.2: Equilibrate the kit to room temperature 20 min in advance, add the diluent that comes with the ELISA kit to the freeze-dried standard, and prepare different standard concentrations (such as 0 pg/ml, 7.8 pg/ml, 15.6 pg/ml, 31.25 pg/ml, 62.5 pg/ml, 125 pg/ml, 250 pg/ml, and 500 pg/ml), take out the plate wells required for the test from the sealed bag, seal the unused plate wells and store them back at 4° C.

Step 3.3. Add the standard and ELISA kit's universal sample diluent to the blank well, add standards of different concentrations to the standard well, and add the specimen to be tested to the sample well, 100 μl per well, then seal the reaction well with the sealing tape that comes with the kit, incubate in a 37° C. incubator in the dark for 90 min.

Step 3.4: Use the biotinylated antibody diluent that comes with the ELISA kit 20 min in advance to dilute the 30× concentrated biotinylated antibody into 1× biotinylated antibody working solution.

Step 3.5: Use the double-distilled water to dilute the concentrated washing solution that comes with the 20×ELISA kit into 1× washing working solution. Pat the liquid in the wells dry on clean thick absorbent paper, add 350 μl 1× washing working solution into the wells, let it stand for 30 seconds, and then pat dry the liquid. Repeat plate washing 5 times.

Step 3.6: Add the biotinylated antibody diluent to the blank wells, add 1× biotinylated antibody working solution to the remaining wells, 100 μl per well, seal the reaction wells with new sealing tape, and incubate in a 37° C. incubator in the dark for 60 min.

Step 3.7: Use the enzyme conjugate diluent that comes with the ELISA kit to dilute the 30× concentrated enzyme conjugate into 1× enzyme conjugate working solution 20 min in advance, and store it at room temperature in the dark.

Step 3.8: Wash the plate according to the method of step 3.5.

Step 3.9: Add enzyme conjugate diluent to the blank wells, add 1× enzyme conjugate working solution to the remaining wells, 100 μl per well, seal the reaction wells with new sealing tape, and incubate in the dark at 37° C. for 30 min.

Step 3.10. Preheat the ELIASA 10 min in advance and set the detection procedure.

Step 3.11: Wash the plate according to the method of step 3.5.

Step 3.12. Add 100 μl chromogenic substrate (TMB) to each well and incubate at 37° C. in the dark for 15 min.

Step 3.13. Add 100 μl of the reaction stop solution that comes with the ELISA kit to each well, mix well and measure the OD450 value immediately (within 3 min).

Step 3.14. According to the concentration of the standard and the corresponding OD value, with the concentration of the standard as the abscissa and the OD value as the ordinate, use a quadratic polynomial equation to fit and draw a standard curve.

Step 3.15. Calculate the corresponding sample concentration on the standard curve based on the OD value of the sample, and perform statistics and analysis on the obtained data by using Graphpad prism and SPSS software, as shown in FIG. 4 to FIG. 6.

Figure 4:
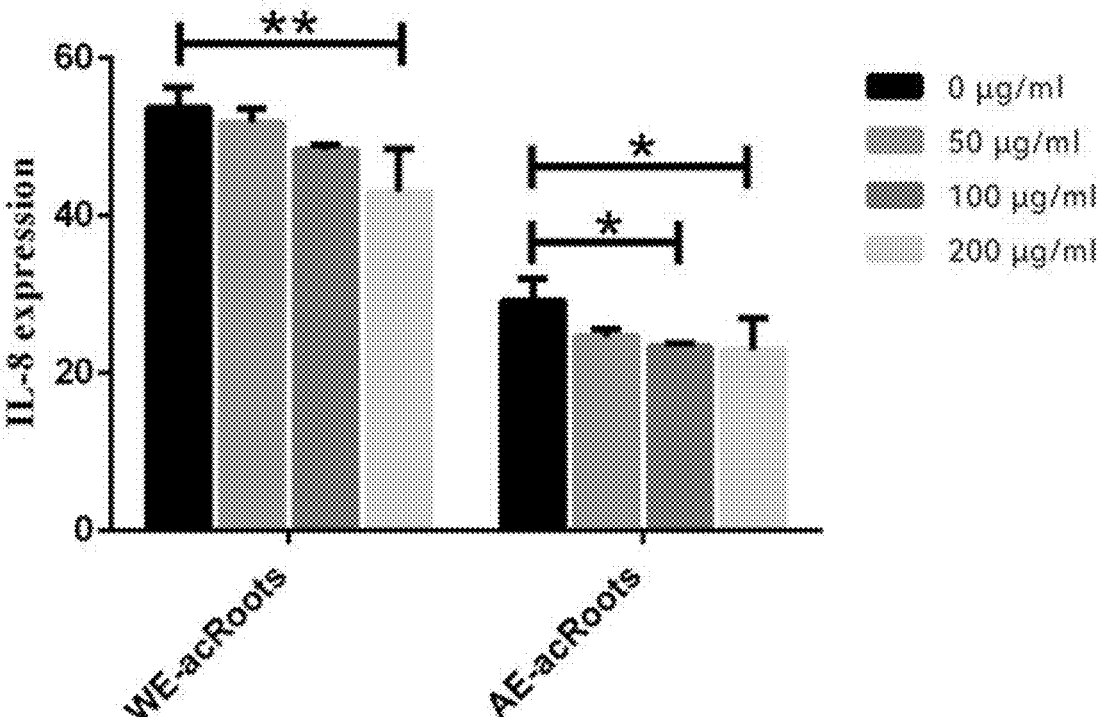
FIG. 4 shows an effect of the radix actinidiae chinensis extract on expression of an inflammatory factor IL-8 in intestinal epithelial cells.
Figure 5:
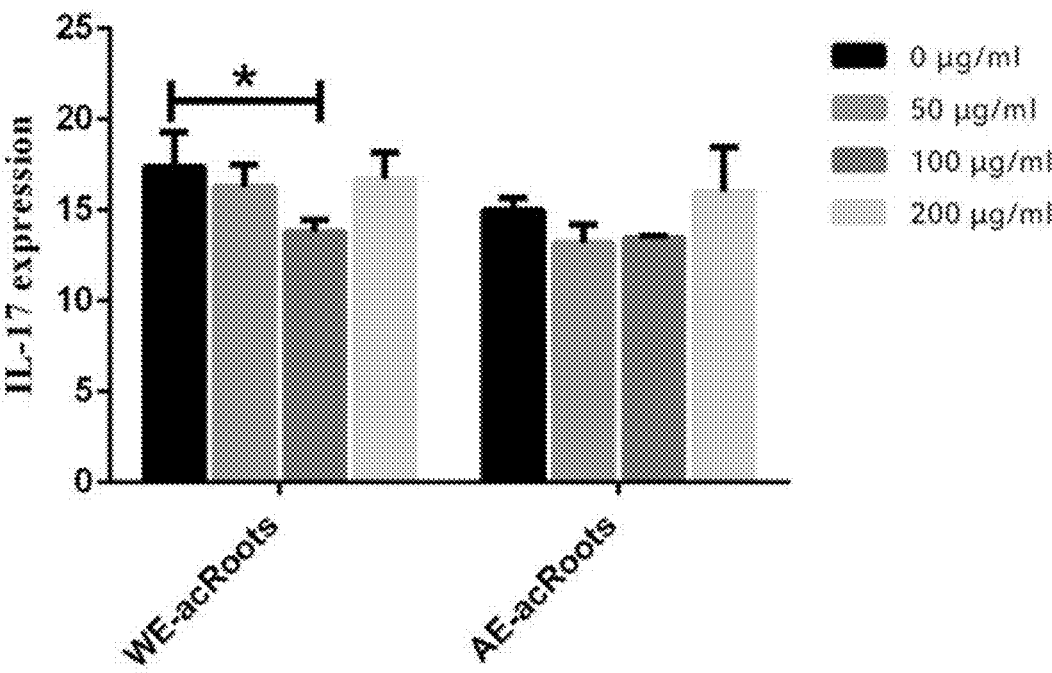
FIG. 5 shows an effect of the radix actinidiae chinensis extract on expression of an inflammatory factor IL-17 in intestinal epithelial cells.
Figure 6:
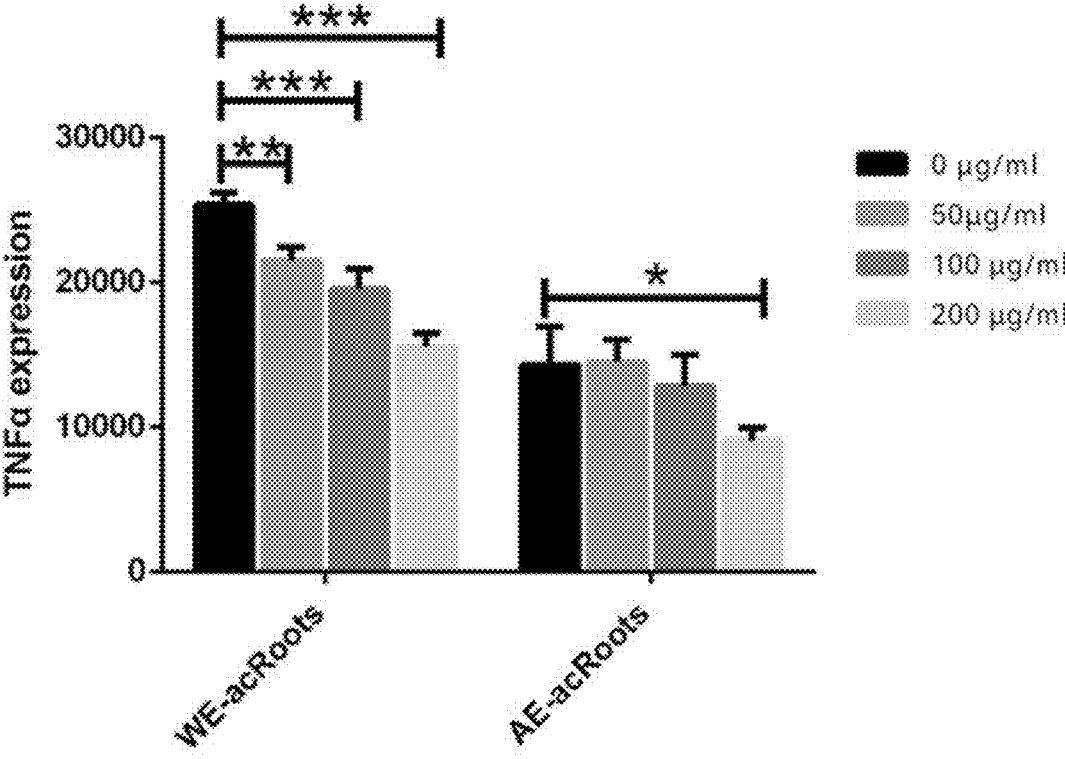
FIG. 6 shows an effect of the radix actinidiae chinensis extract on expression of an inflammatory factor TNFα in intestinal epithelial cells.

The results from FIG. 4 to FIG. 6 show that the treatment with the radix actinidiae chinensis water extract at concentrations of 50 μg/ml, 100 μg/ml and 200 μg/ml can significantly reduce the secretion of inflammatory factors IL-8, IL-17, and TNFα in intestinal epithelial cells; the treatment with the radix actinidiae chinensis alcohol extract at concentrations of 50 μg/ml, 100 μg/ml and 200 μg/ml can significantly reduce the secretion of inflammatory factors IL-8 and TNFα in intestinal epithelial cells; and therefore, it can be proved that the radix actinidiae chinensis water extract and the radix actinidiae chinensis alcohol extract have anti-inflammatory effects.

Embodiment 9

The application of the radix actinidiae chinensis extract in a medicine for treating ulcerative colitis was verified in Embodiment 8 that the radix actinidiae chinensis extract has an obvious anti-inflammatory effect on ulcerative colitis. Therefore, the radix actinidiae chinensis extract is used as a raw material to prepare medicines for treating ulcerative colitis and also has the same inhibitory effect on ulcerative colitis.

The route of administration of the present invention is to decoct the traditional Chinese medicinal material of the radix actinidiae chinensis with water to obtain the radix actinidiae chinensis extract, and then take it orally or use it as an enema, or the route of administration is to take the finished product of the radix actinidiae chinensis extract or dissolve it and then use it as an enema.

Embodiment 10

The application of the radix actinidiae chinensis in a medicine for treating ulcerative colitis was verified in Embodiment 8 that the radix actinidiae chinensis extract has an obvious anti-inflammatory effect on ulcerative colitis, and it can be determined that the radix actinidiae chinensis as the raw material also has an anti-inflammatory effect on ulcerative colitis.

Finally, it should be noted that the above embodiments are only used to illustrate the technical solutions of the present invention and do not limit the protection scope of the present invention. Although the present invention has been described in detail with reference to the preferred embodiments, those of ordinary skill in the art will understand that modifications or equivalent substitutions may be made to the technical solution of the present invention without departing from the essence and scope of the technical solution of the present invention.

What is claimed is:

1. A method for treating ulcerative colitis, comprising a step of administering a radix actinidiae chinensis extract to a subject in need thereof, wherein the radix actinidiae chinensis extract is a radix actinidiae chinensis water extract or a radix actinidiae chinensis alcohol extract; and the radix actinidiae chinensis extract is an only active ingredient in the treating the ulcerative colitis; and the radix actinidiae chinensis extract decreases colorectal shortening, reduces occult blood production, and/or decreases weight loss.

2. The method according to claim 1, wherein when the radix actinidiae chinensis extract is the radix actinidiae chinensis water extract, and the ulcerative colitis is inhibited by decreasing secretion of at least one of an inflammatory factor IL-8, an inflammatory factor IL-17, or an inflammatory factor TNFα in intestinal epithelial cells.

3. The method according to claim 2, wherein the radix actinidiae chinensis extract is dissolved in water, and a concentration of the radix actinidiae chinensis extract is 20 μg/ml to 300 μg/ml.

4. The method according to claim 2, wherein a route of administration is to decoct a traditional Chinese medicinal material of radix actinidiae chinensis with water to obtain the radix actinidiae chinensis extract, and then take the radix actinidiae chinensis extract orally or use the radix actinidiae chinensis extract as an enema; or a route of administration is to take a finished product of the radix actinidiae chinensis extract after mixing the radix actinidiae chinensis extract with water or dissolve the finished product of the radix actinidiae chinensis extract and then use the finished product of the radix actinidiae chinensis extract as an enema.

5. The method according to claim 1, wherein when the radix actinidiae chinensis extract is the radix actinidiae chinensis alcohol extract, and the ulcerative colitis is inhibited by decreasing secretion of at least one of an inflammatory factor IL-8 or an inflammatory factor TNFα in intestinal epithelial cells.

6. The method according to claim 5, wherein the radix actinidiae chinensis extract is dissolved in water, and a concentration of the radix actinidiae chinensis extract is 20 μg/ml to 300 μg/ml.

7. The method according to claim 5, wherein a route of administration is to decoct a traditional Chinese medicinal material of radix actinidiae chinensis with water to obtain the radix actinidiae chinensis extract, and then take the radix actinidiae chinensis extract orally or use the radix actinidiae chinensis extract as an enema; or a route of administration is to take a finished product of the radix actinidiae chinensis extract after mixing the radix actinidiae chinensis extract with water or dissolve the finished product of the radix actinidiae chinensis extract and then use the finished product of the radix actinidiae chinensis extract as an enema.

8. The method according to claim 1, wherein the radix actinidiae chinensis extract is dissolved in water, and a concentration of the radix actinidiae chinensis extract is 20 μg/ml to 300 μg/ml.

9. The method according to claim 1, wherein a route of administration is to decoct a traditional Chinese medicinal material of radix actinidiae chinensis with water to obtain the radix actinidiae chinensis extract, and then take the radix actinidiae chinensis extract orally or use the radix actinidiae chinensis extract as an enema; or a route of administration is to take a finished product of the radix actinidiae chinensis extract after mixing the radix actinidiae chinensis extract with water or dissolve the finished product of the radix actinidiae chinensis extract and then use the finished product of the radix actinidiae chinensis extract as an enema.

* * * * *